(12) United States Patent
Jonas et al.

(10) Patent No.: US 7,449,588 B2
(45) Date of Patent: Nov. 11, 2008

(54) METHODS OF STABILIZING THIOPHENE DERIVATIVES

(75) Inventors: Friedrich Jonas, Aachen (DE); Klaus Wussow, Netphen (DE); Knud Reuter, Krefeld (DE)

(73) Assignee: H.C. Starck GmbH, Goslar (DE)

( * ) Notice: Subject to any disclaimer, the term of this patent is extended or adjusted under 35 U.S.C. 154(b) by 0 days.

(21) Appl. No.: 11/744,264

(22) Filed: May 4, 2007

(65) Prior Publication Data

US 2007/0260070 A1    Nov. 8, 2007

(30) Foreign Application Priority Data

May 4, 2006   (DE) ................ 10 2006 020 744

(51) Int. Cl.
*C07D 333/16*  (2006.01)
*C07D 495/06*  (2006.01)
(52) U.S. Cl. .......................... 549/50; 549/78
(58) Field of Classification Search ............. 549/50, 549/78
See application file for complete search history.

(56) References Cited

U.S. PATENT DOCUMENTS 5,453,211 A * 9/1995 Alward .................. 508/110

6,369,239 B2    4/2002   Rauchschwalbe et al.

FOREIGN PATENT DOCUMENTS

EP        1 142 888      10/2001

* cited by examiner

*Primary Examiner*—Taofiq A Solola
(74) *Attorney, Agent, or Firm*—Connolly Bove Lodge & Hutz LLP

(57) ABSTRACT

Methods of stabilizing thiophene derivatives of the general formula (I) by treatment with basic compounds:

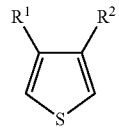

(I)

wherein $R^1$ and $R^2$ each independently represents a moiety selected from the group consisting of hydrogen, optionally substituted $C_{1-20}$ alkyl groups which can contain up to 5 heteroatoms selected from the group consisting of oxygen and sulfur, optionally substituted $C_{1-20}$ oxyalkyl groups which can contain up to 5 heteroatoms selected from the group consisting of oxygen and sulfur, or wherein $R^1$ and $R^2$ together represent a fused cyclic moiety selected from the group consisting of optionally substituted $C_{1-20}$ dioxyalkylene groups and $C_{1-20}$ dioxyarylene groups; and stabilized thiophene derivatives that can be prepared by such methods.

20 Claims, No Drawings

METHODS OF STABILIZING THIOPHENE DERIVATIVES

BACKGROUND OF THE INVENTION

Thiophene derivatives, particularly those which are substituted in the 3-position and/or 4-position by way of an oxygen atom, are suitable initial materials for preparing electrically conductive polythiophenes. For the purpose of achieving high electrical conductivities in this connection, the purity of the thiophene derivatives plays a crucial role. Ordinarily, distillation is used as a conventional purification process for thiophene derivatives.

But it has now become evident that the thiophenes that have been purified in this way have a tendency in the course of storage towards changes in color and/or the formation of undesirable secondary components, such as, for example, the formation of dimers. This results in considerable impairment of the properties of the polythiophenes prepared therefrom.

Consequently there has continued to be a demand for a process for stabilizing such thiophene derivatives, in order to avoid the changes in color or formation of secondary components described in the foregoing, and hence to make thiophene derivatives available that also after storage exhibit sufficient purity for further processing into electrically conductive polythiophenes.

Consequently, one object of the present invention includes providing such a process, and hence, thiophene derivatives of suitable quality.

BRIEF SUMMARY OF THE INVENTION

The invention relates to methods for stabilizing thiophene derivatives, and also to stabilized thiophene derivatives that can be obtained by this process.

Surprisingly, it has now been found that it is possible for thiophene derivatives having the formula (I):

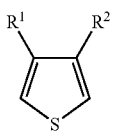

(I)

to be stabilized by treatment with basic compounds after preparation and purification, by distillation for example, and that undesirable changes in color and the formation of secondary components can be avoided.

The present invention includes methods for stabilizing thiophene derivatives having the general formula (I):

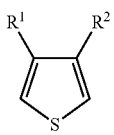

(I)

in which $R^1$ and $R^2$ stand, independently of one another, for hydrogen, for an optionally substituted $C_1$-$C_{20}$-alkyl group or $C_1$-$C_{20}$-oxyalkyl group, optionally interrupted by 1 to 5 oxygen atoms and/or sulfur atoms, or jointly for an optionally substituted $C_1$-$C_{20}$-dioxyalkylene group or $C_1$-$C_{20}$-dioxyarylene group, characterised in that the thiophene derivatives are treated with basic compounds.

DETAILED DESCRIPTION OF THE INVENTION

To be understood as basic compounds within the scope of the invention are those compounds, the 10 wt. % suspension or solution of which in water exhibits a pH value of more than 7, preferably more than 8. The pH value is measured at 20° C. Solids that are insoluble or only very sparingly soluble in the thiophenes to be stabilized are preferably employed as basic compounds.

Alkali hydroxides or alkaline-earth hydroxides, alkali aluminosilicates or alkaline-earth aluminosilicates, main-group-metal oxides or transition-metal oxides or ion-exchange resins are preferably used as basic compounds for the process according to the invention.

Lithium hydroxide, sodium hydroxide, potassium hydroxide, calcium hydroxide, magnesium hydroxide or barium hydroxide may be named, for example, as suitable alkali hydroxides and alkaline-earth hydroxides.

Calcium oxide, magnesium oxide, barium oxide, aluminium oxide, bismuth oxide, tin oxide, lead oxide or zinc oxide may be named, for example, as suitable main-group-metal oxides, with zinc oxide, as an oxide of a transition metal, being assigned to this group by reason of its properties which are similar to those of a main-group oxide. Suitable main-group-metal oxides also optionally include the oxide hydroxides thereof.

By way of alkali aluminosilicates or alkaline-earth aluminosilicates, those having the general formula (A) may be named, for example:

$$M_{2/z} \cdot Al_2O_3 \cdot xSiO_2 \cdot yH_2O \qquad (A)$$

wherein M stands for a univalent or multivalent alkali metal or alkaline-earth metal, H or $NH_4$; z stands for the valency of the cation; x stands for a number from 1.8 to 12; and y stands for a number from 0 to 8, not just including integers.

By way of transition-metal oxides, those of the metals iron, copper, nickel, cobalt, manganese, molybdenum, niobium, titanium, tantalum, tungsten, or optionally the oxide hydroxides thereof may be named in exemplary manner.

By way of ion-exchange resins, those may be named in exemplary manner which exhibit functional basic groups such as, for example, primary, secondary or tertiary amine groups or quaternary ammonium groups. The ion-exchangers may vary in their basicity, according to the type and combination of the functional groups. For example, strongly basic ion-exchangers usually contain quaternary ammonium groups, whereas weakly basic ion-exchangers frequently carry the less-basic primary, secondary and/or tertiary amine groups. However, between strongly basic and weakly basic ion-exchangers arbitrary mixed forms are also known.

Calcium oxide, magnesium oxide, barium oxide, aluminium oxide or optionally the oxide hydroxides thereof are used in particularly preferred manner as basic compounds within the scope of the invention.

The basic compounds may be employed in commercially available form, i.e. powder, granulate, beads etc., and require no further purification or treatment.

The basic compounds may optionally be used in combination with further compounds acting absorptively, such as, for example, activated carbon. Use is preferably made of neutral or basically treated activated carbon.

Thiophene derivatives within the scope of the invention are preferably those having the general formula (II):

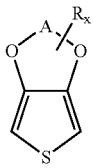

(II)

wherein

A stands for an optionally substituted $C_1$-$C_5$-alkylene residue or a $C_1$-$C_{12}$-arylene residue, preferably for an optionally substituted $C_2$-$C_3$-alkylene residue;

R stands for a linear or branched, optionally substituted $C_1$-$C_{18}$-alkyl residue, preferably a linear or branched, optionally substituted $C_1$-$C_{14}$-alkyl residue, an optionally substituted $C_5$-$C_{12}$-cycloalkyl residue, an optionally substituted $C_6$-$C_{14}$-aryl residue, an optionally substituted $C_7$-$C_{18}$-aralkyl residue, an optionally substituted $C_1$-$C_4$-hydroxyalkyl residue, preferably an optionally substituted $C_1$-$C_2$-hydroxyalkyl residue, or a hydroxyl residue;

X stands for an integer from 0 to 8, preferably from 0 to 6, particularly preferably for 0 or 1; and in the case where several residues R are bonded to A, these may be the same or different.

The general formula (II) is to be understood in such a way that the substituent R may be bonded x times to the alkylene residue or arylene residue A.

Particularly preferred thiophene derivatives within the scope of the invention are those having the general formula (IIa)

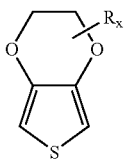

(IIa)

in which R and x have the significance stated for general formula (II).

In a preferred embodiment of the invention the thiophene derivative is 3,4-ethylenedioxythiophene.

$C_1$-$C_5$-alkylene residues A within the scope of the invention are methylene, ethylene, n-propylene, n-butylene or n-pentylene. $C_1$-$C_{12}$-arylene residues A within the scope of the invention may be, for example, phenylene, naphthylene, benzylidene or anthracenylidene. $C_1$-$C_{18}$ alkyl within the scope of the invention stands for linear or branched $C_1$-$C_{18}$-alkyl residues, such as, for example, methyl, ethyl, n-propyl, isopropyl, n-butyl, isobutyl, sec-butyl, tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadcyl or n-octadecyl. $C_1$-$C_{20}$-alkyl groups furthermore include, for example, n-nonadecyl and n-eicosyl. $C_5$-$C_{12}$ cycloalkyl within the scope of the invention stands for $C_5$-$C_{12}$-cycloalkyl residues, such as, for example, cyclopentyl, cyclohexyl, cycloheptyl, cyclooctyl, cyclononyl or cyclodecyl; $C_5$-$C_{14}$ aryl for $C_5$-$C_{14}$-aryl residues, such as, for example, phenyl or naphthyl; and $C_7$-$C_{18}$ aralkyl for $C_7$-$C_{18}$-aralkyl residues, such as, for example, benzyl, o-tolyl, m-tolyl, p-tolyl, 2,3-xylyl, 2,4-xylyl, 2,5-xylyl, 2,6-xylyl, 3,4-xylyl, 3,5-xylyl or mesityl. $C_1$-$C_{20}$ oxyalkyl within the scope of the invention stands for $C_1$-$C_{20}$-oxyalkyl residues, such as, for example, methoxy, ethoxy, n-propoxy, isopropoxy, n-butoxy, isobutoxy, sec-butoxy, tert-butoxy, n-pentyloxy, 1-methylbutyloxy, 2-methylbutyloxy, 3-methylbutyloxy, 1-ethylpropyloxy, 1,1-dimethylpropyloxy, 1,2-dimethylpropyloxy, 2,2-dimethylpropyloxy, n-hexyloxy, n-heptyloxy, n-octyloxy, 2-ethylhexyloxy, n-nonyloxy, n-decyloxy, n-undecyloxy, n-dodecyloxy, n-tridecyloxy, n-tetradecyloxy, n-hexadcyloxy, n-nonadecyloxy or n-eicosyloxy. The preceding list serves for exemplary elucidation of the invention and is not to be regarded as being definitive.

Numerous organic groups enter into consideration as optionally further substituents of the alkylene residues or arylene residues A; for example, alkyl, cycloalkyl, aryl, halogen, ether, thioether, disulfide, sulfoxide, sulfone, sulfonate, amino, aldehyde, keto, carboxylic-ester, carboxylic-acid, carbonate, carboxylate, cyano, alkylsilane, alkoxysilane and carboxylamide groups.

To the extent that the thiophene derivative exhibits one or more stereocentres, the thiophene derivative may be a racemate, an enantiomerically pure or diastereomerically pure compound, or an enantiomerically enriched or diastereomerically enriched compound. The expression "enantiomerically enriched compound" is to be understood to mean a compound with an enantiomeric excess (ee) of more than 50%. The expression 'diastereomerically enriched compound' is to be understood to mean a compound with a diastereomeric excess (de) of more than 30%. According to the invention, however, it may also be a question of an arbitrary mixture of diastereomers.

The thiophene derivatives having the general formula (I), (II), or (IIa) are capable of being prepared by processes known to a person skilled in the art. Such a preparation process is described in EP-A 1 142 888, for example, the entire contents of which are herein incorporated by reference.

Relative to the weight of the thiophene derivative, use is made of 0.01 wt. % to 50 wt. %, preferably 0.1 wt. % to 10 wt. %, particularly preferably 0.5 wt. % to 5 wt. %, of the basic compound or of the mixture of basic compound and further compound acting absorptively.

The treatment of the thiophene derivatives with the basic compounds, optionally in a mixture with the further absorptive compound, may be undertaken, for example, by addition of these compounds to the thiophene derivatives, by stirring, and by subsequent separation of the basic compound and optionally absorptive compound by filtering.

The treatment may also be undertaken in such a manner that the basic compound, optionally in a mixture with the further absorptive compound, is charged into a suitable filter unit or column and subsequently the thiophene derivative is conducted over the thiophene derivative and optionally further absorptive compound. On an industrial scale, this process has the advantage, for example, that the additional filtration is eliminated.

The duration of the treatment of the thiophene derivatives may last from a few seconds up to several hours.

The treatment of the thiophene derivatives with the basic compounds may be undertaken at temperatures from −10° C. to 150° C. The treatment is preferably undertaken at room temperature.

The thiophene derivatives that have been stabilized with the process according to the invention tend distinctly less towards changes in color and/or formation of secondary components, and therefore have a distinctly higher stability in storage. In their properties they differ significantly from the thiophene derivatives that have not been stabilized in accordance with the process of the invention.

Consequently the stabilized thiophene derivatives that can be obtained by the process according to the invention are likewise a subject of the present invention.

The invention will now be described in further detail with reference to the following non-limiting example.

EXAMPLE

Example 1

2 g basic aluminium oxide (Aldrich, pH value in aqueous solution 9.5±0.5, particle size about 150 mesh) were charged into a glass column (length 20 cm, diameter 1 cm) sealed at the bottom by a glass frit. 50 g of freshly distilled 3,4-ethylenedioxythiophene were poured over the aluminium oxide. The treated 3,4-ethylenedioxythiophene was charged into a 100 ml glass flask.

Furthermore, 50 g of the freshly distilled 3,4-ethylenedioxythiophene without the treatment according to the invention with the basic aluminium oxide were charged into a 100 ml glass flask. Both specimens were stored under identical conditions.

Subsequently the changes in color of the treated specimen in comparison with the untreated specimen were observed in the course of time.

After four weeks the untreated specimen was distinctly more strongly yellow-colored than the specimen treated with aluminium oxide.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of stabilizing thiophene derivatives comprising:
   (a) providing a thiophene derivative of the general formula (I):

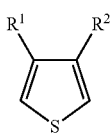

(I)

wherein $R^1$ and $R^2$ each independently represents a moiety selected from the group consisting of hydrogen, optionally substituted $C_{1-20}$ alkyl groups which can contain up to 5 heteroatoms selected from the group consisting of oxygen and sulfur, optionally substituted $C_{1-20}$ oxyalkyl groups which can contain up to 5 heteroatoms selected from the group consisting of oxygen and sulfur, or wherein $R^1$ and $R^2$ together represent a fused cyclic moiety selected from the group consisting of optionally substituted $C_{1-20}$ dioxyalkylene groups and $C_{1-20}$ dioxyarylene groups; and
   (b) treating the thiophene derivative with a basic compound.

2. The method according to claim 1, wherein the basic compound comprises one or more selected from the group consisting of alkali hydroxides, alkaline-earth hydroxides, alkali aluminosilicates, alkaline-earth aluminosilicates, main-group metal oxides, transition-metal oxides, ion-exchange resins and mixtures thereof.

3. The method according to claim 1, wherein the basic compound comprises one or more compounds selected from the group consisting of calcium oxide, magnesium oxide, barium oxide, aluminium oxide, oxide hydroxides thereof and mixtures thereof.

4. The method according to claim 1, further comprising treating the thiophene derivative with an absorptive compound.

5. The method according to claim 4, wherein the absorptive compound comprises activated carbon.

6. The method according to claim 3, further comprising treating the thiophene derivative with an absorptive compound.

7. The method according to claim 6, wherein the absorptive compound comprises activated carbon.

8. The method according to claim 1, wherein the thiophene derivative corresponds to the general formula (II):

(II)

wherein A represents a moiety selected from the group consisting of optionally substituted $C_{1-5}$ alkylene moieties and optionally substituted $C_{1-12}$ arylene moieties, x represents an integer of 0 to 8, and each R independently represents a hydroxyl group or a linear or branched, optionally substituted moiety selected from the group consisting of $C_{1-18}$ alkyl moieties, $C_{5-12}$ cycloalkyl moieties, $C_{6-14}$ aryl moieties, $C_{7-18}$ aralkyl moieties, and $C_{1-4}$ hydroxyalkyl residues.

9. The method according to claim 8, wherein A represents an optionally substituted $C_2$ alkylene moiety.

10. The method according to claim 8, wherein x is 0 or 1.

11. The method according to claim 9, wherein x is 0 or 1.

12. The method according to claim 1, wherein the thiophene derivative comprises 3,4-ethylenedioxythiophene.

13. The method according to claim 8, wherein the basic compound comprises one or more selected from the group consisting of alkali hydroxides, alkaline-earth hydroxides, alkali aluminosilicates, alkaline-earth aluminosilicates, main-group metal oxides, transition-metal oxides, ion-exchange resins and mixtures thereof.

14. The method according to claim 8, wherein the basic compound comprises one or more compounds selected from the group consisting of calcium oxide, magnesium oxide, barium oxide, aluminium oxide, oxide hydroxides thereof and mixtures thereof.

15. The method according to claim 10, wherein the basic compound comprises one or more compounds selected from the group consisting of calcium oxide, magnesium oxide, barium oxide, aluminium oxide, oxide hydroxides thereof and mixtures thereof.

16. The method according to claim 8, further comprising treating the thiophene derivative with an absorptive compound.

17. The method according to claim 14, wherein the absorptive compound comprises activated carbon.

18. A method of stabilizing thiophene derivatives comprising:

(a) providing a thiophene derivative corresponding to the general formula (II):

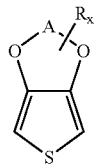

(II)

wherein A represents an optionally substituted $C_{2-3}$ alkylene moiety, x represents 0 or 1, and each R independently represents a hydroxyl group or a linear or branched, optionally substituted moiety selected from the group consisting of $C_{1-18}$ alkyl moieties, $C_{5-12}$ cycloalkyl moieties, $C_{6-14}$ aryl moieties, $C_{7-18}$ aralkyl moieties, and $C_{1-4}$ hydroxyalkyl moieties; and (b) treating the thiophene derivative with activated carbon and a basic compound selected from the group consisting of calcium oxide, magnesium oxide, barium oxide, aluminium oxide, oxide hydroxides thereof and mixtures thereof.

19. A stabilized thiophene derivative prepared by the method according to claim 1.

20. A stabilized thiophene derivative prepared by the method according to claim 18.

* * * * *